US00PP24371P3

(12) United States Plant Patent
Bak et al.

(10) Patent No.: US PP24,371 P3
(45) Date of Patent: Apr. 1, 2014

(54) ***VRIESEA* PLANT NAMED 'VENGA'**

(50) Latin Name: ***Vriesea* sp.**
Varietal Denomination: VENGA

(75) Inventors: Elly Bak, Rijsenhout (NL); Nicolaas D. M. Steur, Oude Niedorp (NL)

(73) Assignee: Corn.Bak B.V., Assendelft (NE)

( * ) Notice: Subject to any disclaimer, the term of this patent is extended or adjusted under 35 U.S.C. 154(b) by 119 days.

(21) Appl. No.: 13/506,345

(22) Filed: Apr. 13, 2012

(65) Prior Publication Data

US 2013/0276191 P1 Oct. 17, 2013

(51) Int. Cl.
*A01H 5/00* (2006.01)

(52) U.S. Cl.
USPC ..... Plt./370

(58) Field of Classification Search
USPC ..... Plt./370
See application file for complete search history.

(56) References Cited

U.S. PATENT DOCUMENTS

PP18,176 P3 * 10/2007 Bak et al. ..... Plt./371

OTHER PUBLICATIONS

Printout of application information from Community Plant Variety Office (CPVO) website for corresponding CPVO application No. 2011/2616 filed Nov. 3, 2011 (1 page) (http://www.cpvoextranet.cpvo.europa.eu).

* cited by examiner

*Primary Examiner* — Wendy C Haas
(74) *Attorney, Agent, or Firm* — Foley & Lardner LLP

(57) ABSTRACT

A new and distinct *Vriesea* plant named 'VENGA' characterized as a funnel form rosette plant, measuring about 40 cm to 45 cm in height (when flowering) and 45 cm in diameter, producing compound, red in color (RHS 45A), bipinnate spike inflorescence, measuring about 30-35 cm in height and about 18 cm in diameter, about 7 to 9 branches, and yellow-green foliage, measuring about 25-30 cm in length and about 4.5 cm to 5 cm in width.

1 Drawing Sheet

Latin name of the genus and species of the plant claimed: *Vriesea* sp.

Variety denomination: 'VENGA'.

BACKGROUND OF THE INVENTION

The present invention relates to a new and distinct cultivar of *Vriesea* plant, botanically known as *Vriesea* sp., hereinafter referred to by the cultivar name 'VENGA'. The genus of *Vriesea* belongs to the Bromeliaceae family.

The new *Vriesea* cultivar is a product of a planned breeding program conducted by the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'VENGA' originated from a cross-made in a controlled breeding program by the inventors in 1997 in Assendelft, The Netherlands. The female or seed parent is a *Vriesea* selection designated '93430' (unpatented). The male or pollen parent is a *Vriesea* selection designated '91209' (unpatented). 'VENGA' was discovered and selected by the inventors in June of 2002, as a single flowering plant within the progeny of the stated cross in a controlled environment in Assendelft, The Netherlands.

Asexual reproduction of the new cultivar 'VENGA' performed by vegetative means by tissue culture was first performed in 2007, in Assendelft, The Netherlands. The first 'VENGA' plants propagated through the use of tissue culture flowered in 2009, in Assendelft, The Netherlands, and have demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be unique characteristics of 'VENGA' which in combination distinguish this *Vriesea* as a new and distinct cultivar:

1. Funnel form rosette plant, measuring about 40-45 cm in total height (when flowering) and about 45 cm in diameter;
2. Compound, red (RHS 45A) bipinnate spike inflorescence, measuring about 30-35 cm in height, and about 18 cm in diameter.
3. About 7 to 9 branches,
4. Yellow green foliage, measuring 25-30 cm in length and 4.5 cm to 5.0 cm in width.

Plants of the parents, '93430' (unpatented) and '91209' (unpatented), are no longer available to provide a botanical comparison with the new *Vriesea* cultivar 'VENGA'. The new cultivar 'VENGA'; differs primarily from plants of the parental cultivars by exhibiting a more branched inflorescence, red in color Of the many commercial cultivars known to the present inventors, the most similar in comparison to the new *Vriesea* cultivar 'VENGA' is the *Vriesea* cultivar designated 'STYLE'(U.S. Plant Pat. No. 18,176). Plants of the new cultivar 'VENGA' differ from plants of 'STYLE' primarily in inflorescence color and number of branches ('STYLE' has fewer branches).

BRIEF DESCRIPTION OF THE PHOTOGRAPH

The accompanying photograph illustrates the overall appearance of the new *Vriesea* cultivar 'VENGA' showing the colors as true as is reasonably possible with colored reproductions of this type. Colors in the photograph may differ slightly from the color values cited in the detailed botanical description which accurately describes the color of 'VENGA'.

FIG. 1 shows a side perspective view of a typical potted flowering plant of 'VENGA' at about 18 months of age from potting.

DETAILED BOTANICAL DESCRIPTION

'VENGA' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Vriesea* cultivar as grown in a greenhouse in Assendelft, The Netherlands, under conditions which closely approximate those generally used in commercial practice. Plants of 'VENGA' were grown in a greenhouse with day temperatures ranging from 20° C. to 28° C. and night temperatures ranging from 18° C. to 28° C. No artificial lighting or photoperiodic treatments were conducted, but plants of 'VENGA' are forced into flowering. The following fertilizer is added when growing plants of 'VENGA': 1 part nitrogen, 0.6 parts phosphor, 2 parts Kalium and 0.1 parts magnesium.

Color references are made to The Royal Horticultural Society Colour Chart (R.H.S.), except where general colors of ordinary significance are used. Color values were taken under daylight conditions in a greenhouse in Assendelft, The Netherlands. The age of the plants of 'VENGA' described is about 18 months from potting.

Classification:

*Botanical.*—*Vriesea* sp.

Parentage:

*Male parent.*—*Vriesea* sp. cultivar designated '93430' (unpatented).

*Female parent.*—*Vriesea* sp. cultivar designated '91209' (unpatented).

Propagation: Tissue culture.

Plant:

*General appearance and form.*—Height: About 40-45 cm (when flowering). Width: About 45 cm. Shape: Funnel form rosette. Growth habit: Stemless. Plant Vigor: Good. Flowering Season: A fully grown plant can flower year round, starting 17 to 19 weeks after induction of natural light or trough flowering treatment. Cold Tolerance: Frost tender. Temperatures below 5° C. may damage plants. Fragrance: None.

Foliage:

*Quantity.*—About 25 to 30.

*Size of mature leaf.*—Length: About 25-35 cm. Width: About 4.5-5 cm

*Overall shape.*—Broad and linear.

*Apex shape.*—Abruptly acuminate. .

*Base shape.*—Strap-like around central axis.

*Margin.*—Entire.

*Texture.*—Smooth and glabrous.

*Color.*—Leaf color can vary depending on growing conditions. Upper Surface: Mature leaf: Yellow-green, RHS 147A. Immature leaf: Yellow-green, RHS 147A. Lower Surface: Mature leaf: Yellow-green, RHS 147B. Immature leaf: Yellow-green, RHS 147B.

Inflorescence:

*Quantity and form.*—1 flower per floral bract, typical for the genus *Vriesea*; flowering is normally in progression from base to tip of scape.

*Shape.*—Bipinnate spike (main spike about 12 cm in length and about 7 cm in width, side spike about 11 cm in length and about 6 cm in width).

*Size.*—Height: about 30-35 cm. Diameter: about 18 cm.

*Color.*—Red, RHS 45A.

*Corolla.*—Form: Long and narrow, petals and sepals fused at the base around the ovary. Number: About 70-90 depending on the size of the plant.

*Petals.*—Number: 3 per flower. Length: About 5 cm. Width: About 0.8 cm. Overall Shape: Ligulate. Apex Shape: Obtuse. Base Shape: Fused. Color: Upper surface: Yellow, RHS 8A. Lower surface: Yellow, RHS 8A.

*Sepals.*—Number: 3 per flower. Length: About 3 cm. Width: About 1 cm. Overall Shape: Ligulate. Apex Shape: Acute. Base Shape: Fused. Color: Translucent, Yellow, closest to RHS 8C.

*Branches.*—Quantity: About 7-9. Length: About 11-12 cm. Width: About 6-7 cm. Color: Red, RHS 45A.

*Bracts.*—Quantity of bracts on main spike: About 15. Arrangement: Alternate. Size: Length: About 4-5.5 cm. Width: About 2-4 cm. Overall shape: Ovate. Color: Red, RHS 45A.

Reproductive organs:

*Androecium.*—Stamen: Number: 6 per flower. Length: About 4.5 cm. Diameter: About 0.1 cm. Color: Yellow, RHS 11D. Anther: Length: About 0.6 cm. Color: Yellow, RHS 11C. Pollen: Amount: Scarce. Color: Yellow, too small to qualify R.H.S.

*Gynoecium.*—Pistil: Number: 1 per flower. Length: About 5 cm. Stigma: Shape: 3-parted. Width: About 0.4 cm. Color: Yellow-green, RHS 144B. Style: Length: About 4.5 cm. Color: Yellow, RHS 11D. Ovary: Shape: Conical. Length: About 0.8 cm. Diameter: About 0.3 cm. Color: Yellow, RHS 11D.

Disease/pest resistance: No information is currently available.

Disease/pest susceptibility: No information is currently available.

We claim:

1. A new and distinct *Vriesea* plant named 'VENGA', substantially as illustrated and described herein.

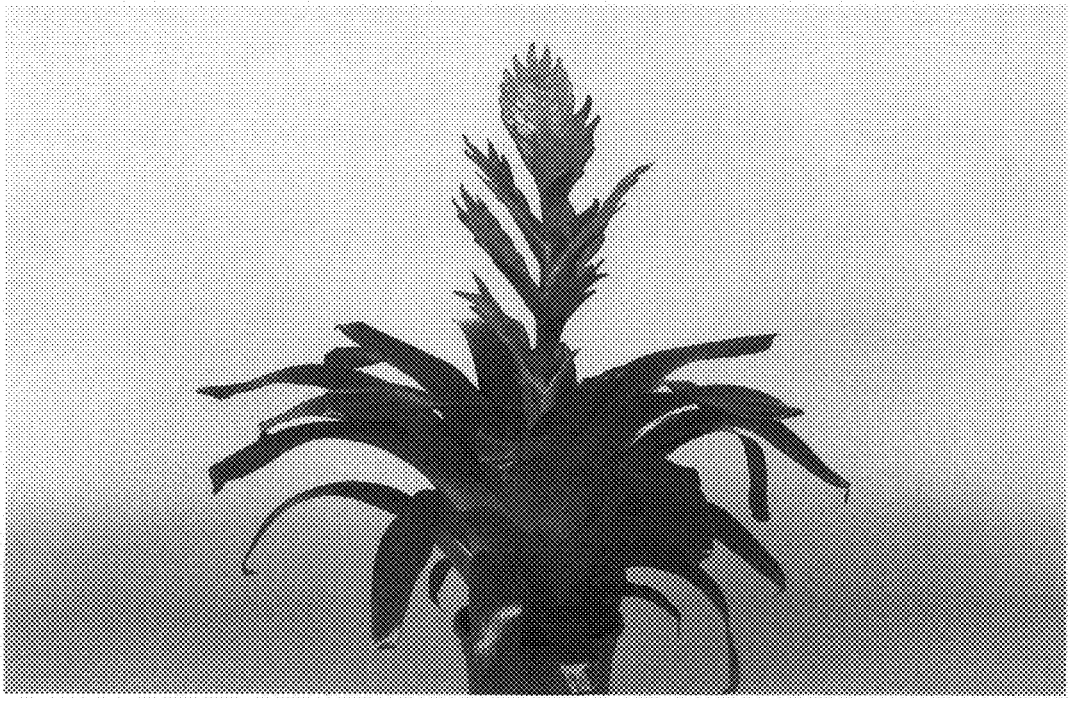

* * * * *